United States Patent
Doi

(10) Patent No.: US 6,559,656 B2
(45) Date of Patent: May 6, 2003

(54) PERMITTIVITY MEASUREMENT OF THIN FILMS

(75) Inventor: Yutaka Doi, Minnetonka, MN (US)

(73) Assignee: Honeywell Advanced Circuits, Inc., Minnetonka, MN (US)

( * ) Notice: Subject to any disclaimer, the term of this patent is extended or adjusted under 35 U.S.C. 154(b) by 0 days.

(21) Appl. No.: 09/752,638

(22) Filed: Dec. 28, 2000

(65) Prior Publication Data

US 2002/0118026 A1 Aug. 29, 2002

(51) Int. Cl.[7] ............................................... G01R 27/28
(52) U.S. Cl. ........................ 324/636; 324/661; 324/675
(58) Field of Search ........................ 333/202; 324/636, 324/637, 672, 675, 679, 757, 661

(56) References Cited

U.S. PATENT DOCUMENTS

| | | | | |
|---|---|---|---|---|
| 4,380,747 A | * | 4/1983 | Curtinot et al. ............. | 333/202 |
| 5,010,301 A | * | 4/1991 | Leung et al. ................ | 324/376 |
| 5,744,970 A | * | 4/1998 | Kim et al. ................... | 324/636 |
| 5,861,757 A | * | 1/1999 | Hougham et al. .......... | 324/672 |
| 6,147,503 A | * | 11/2000 | Nelson et al. .............. | 324/637 |
| 6,281,693 B1 | * | 8/2001 | Fukuda ....................... | 324/757 |

OTHER PUBLICATIONS

Hewlett Packard, Material Measurement Basics, on or before Jul. 28, 1999, pp. 1–25.

Hewlett Packard, Transmission Line Technique, on or before Jul. 28, 1999, pp. 1–30.

* cited by examiner

*Primary Examiner*—N. Le
*Assistant Examiner*—Walter Benson
(74) *Attorney, Agent, or Firm*—Rutan & Tucker, LLP; Robert D. Fish; David J. Zoctewey

(57) ABSTRACT

Measurement of the permittivity of thin films is facilitated through the use of a short cylindrical metal cavity containing parallel plates between which a specimen to be measured is placed. The use of such parallel plates contained within such a cavity is particularly advantageous when swept frequency measurement methods utilizing frequency ranges from 0 to 20 GHz are employed. A test fixture which is preferred for use in providing such a cavity is disclosed as are methods of using the test fixture.

19 Claims, 2 Drawing Sheets

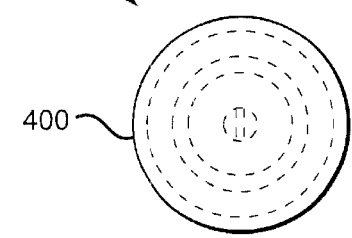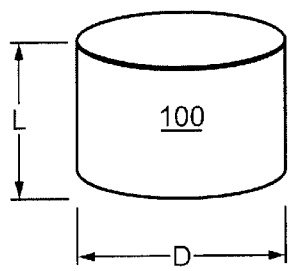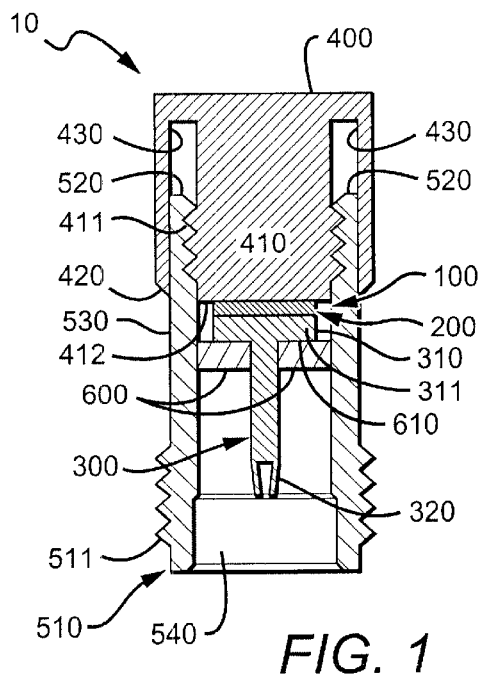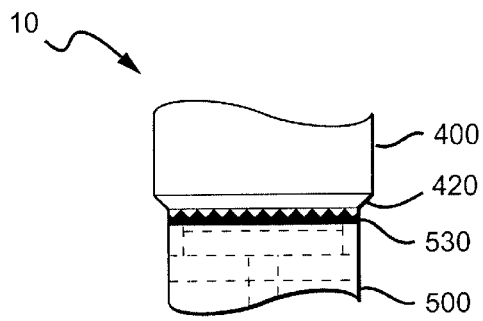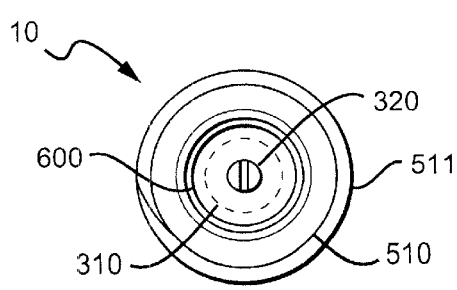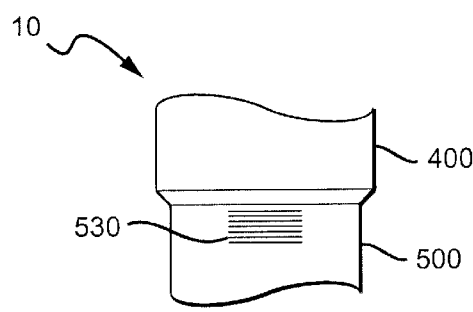

PERMITTIVITY MEASUREMENT OF THIN FILMS

FIELD OF THE INVENTION

The field of the invention is permittivity measurement methods and devices.

BACKGROUND OF THE INVENTION

The permittivity of a specimen is the complex ratio of the capacitance between a pair of electrodes which sandwich the specimen and that of the same pair with an air gap. Measurement of capacitance and determination of permittivity is generally accomplished through the use of a test fixture coupled to a measurement instrument such as an LCR meter, an impedance/material analyzer, or a network analyzer.

Test fixtures may be classified according to the measurement technique which they employ, and thus may be classified as being a parallel plate fixture, coaxial probe, transmission line fixture, free-space fixture, or a resonant cavity fixture. Parallel plate fixtures provide two parallel plates which are essentially electrodes between which a specimen is placed for measurement. Although such fixtures have many desirable characteristics, they are not suitable for measurement using signal frequencies greater than 1.8 GHz. Although other types of fixtures are suitable for use for frequencies greater than 1.8 GHz, their use is often undesirable for other reasons.

As an example, coaxial probe devices essentially transmit a signal into a specimen and examine any reflected portion of the signal picked up by the probe. Unfortunately, because of the need for the material to reflect back a significant portion of the signal, coaxial probes are generally not suitable for thin specimens (i.e. less than or equal to 1 cm). Transmission line fixtures are also problematic because they require that a specimen be shaped to fit within a transmission line such as a wave guide or a coaxial transmission line so that the effects of the specimen on a signal transmitted through the line can be examined. Free space systems broadcast a signal at a specimen through free space and examine the effect of the specimen on the signal. The use of such systems generally require that the specimen be large, flat, thin, and parallel faced, and requires tight control of the distance between an antenna to a sample. Resonant cavity fixtures are similar to transmission line fixtures in that a precisely shaped specimen is placed within a resonant cavity or a transmission line and the effects of the specimen on fields within the cavity/line are examined. As with transmission line fixtures, having to precisely shape a specimen is generally not a desirable aspect of use of the fixture.

Due to the inadequacies described for non-parallel plate fixtures, it is desirable that new parallel plate fixtures which permit the use of frequencies greater than 1.8 GHz be developed.

SUMMARY OF THE INVENTION

The present invention is directed to methods and apparatus which facilitate the measurement of the permittivity of thin films using a parallel plate device for frequencies greater than 1.8 GHz. More specifically, the use of a short cylindrical metal cavity enclosing two parallel plates/surfaces is used as a fixture for permittivity measurement of thin film. The use of such a cavity is particularly advantageous when swept frequency measurement methods utilizing frequency ranges from 0 to 20 GHz are employed.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

FIG. 1 is a cutaway side view of a test fixture embodying the invention.

FIG. 2 is a bottom view of a test fixture embodying the invention;

FIG. 3 is a top view of a test fixture embodying the invention;

FIG. 4 is a side view of a test fixture embodying the invention;

FIG. 5 is a side view of a test fixture embodying the invention;

FIG. 6 is a perspective schematic illustration of a cavity.

DETAILED DESCRIPTION

It is contemplated that positioning a specimen between parallel plates within a metal cavity which has a resonant frequency higher than the frequency of the signal being used to measure the capacitance of the specimen will help prevent inaccuracies which are typically experienced during high frequency capacitance measurements.

Figure 7:
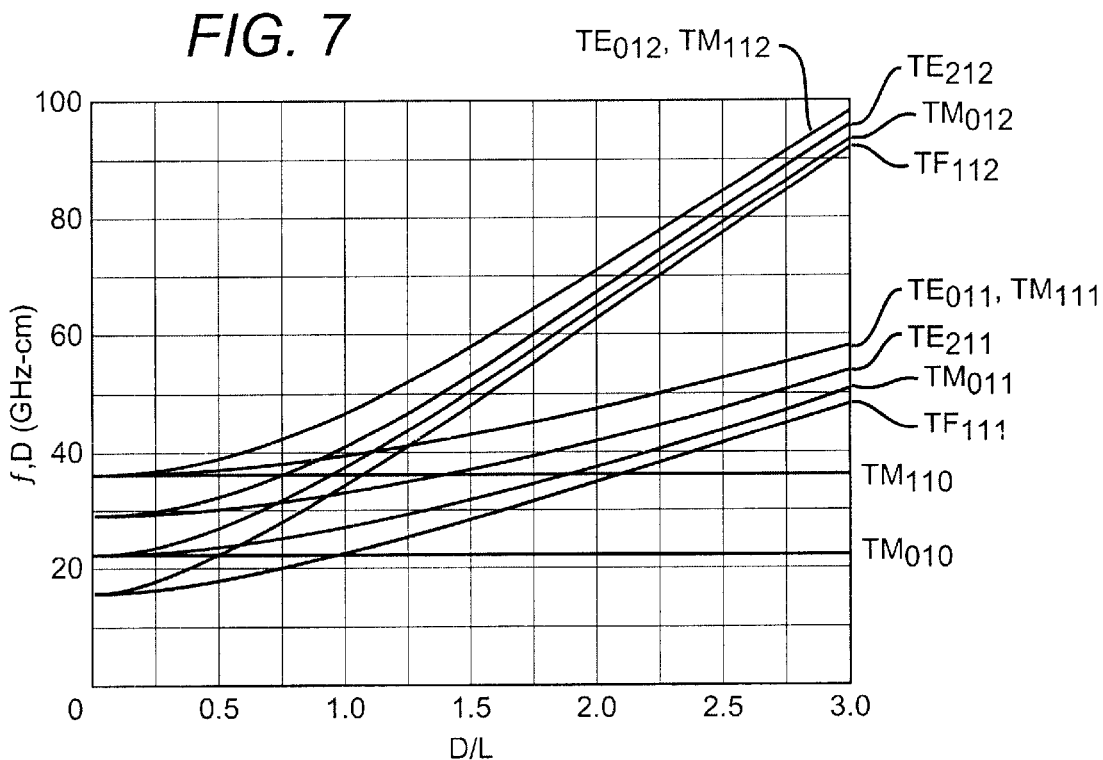
FIG. 7 is a graph of various curves illustrating the relationship of $f_r D$ to D/L.

In FIG. 7, each curve or line indicates the relation between the product $f_r D$ of the resonant frequency, $f_r$, in GHz and the diameter, D, in cm, and the ratio of the diameter of the cylinder, D, to the length of the cylinder, D/L. (FIG. 6 illustrates how D and L correspond to cylinder 100.) In FIG. 7, TE stands for the transverse electric fields and means that there is no longitudinal field (electric), while TM stands for the transverse magnetic fields with no longitudinal magnetic field. The word "longitudinal" refers to the length of the cylinder. The suffixes indicates modes n, m, and p which are the integral number of circumferential turns, the ordinal number of the roots of the radial derivative of the field, and the integral number of the half wave lengths in the longitudinal direction respectively.

The following equation, in which $K_{nm}=\pi/m^{th}$ root of the derivative (radial) of the field, and $\epsilon_r$ and $\mu_r$ are relative permittivity and permeability respectively, can be used to determine the resonant frequency of cylinder 100 and was used to obtains the curves of FIG. 7:

$$f_r D = \frac{3 \times 10^{10}}{\sqrt{\epsilon_r \mu_r}} \sqrt{\left(\frac{1}{K_{nm}}\right)^2 + \left(\frac{Dp}{2L}\right)^2}$$

Figure 8:
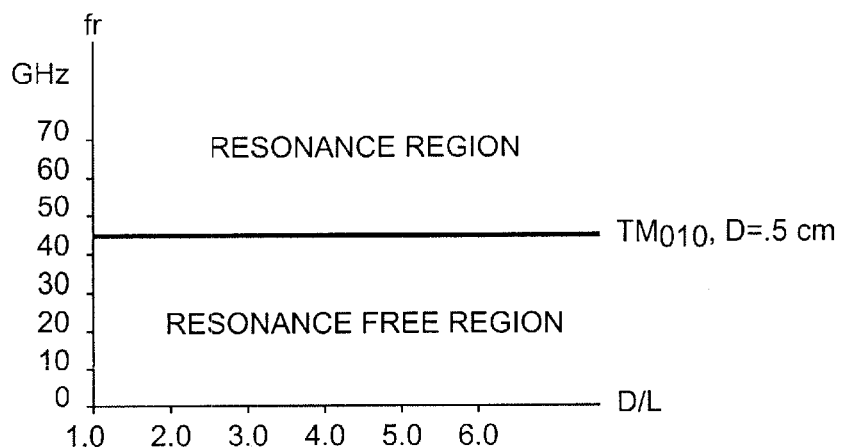
FIG. 8 is a graph of $TM_{010}$ where D=0.5 cm.

In free space, $\epsilon_r = \mu_r = 1$, so, for $TM_{010}$ where D=0.5 cm, p=0 and $K_{01}=1.306^2$, $f_r D=1.3 \times 10^{10}/1.306=2.971 \times 10^{10}$ cm-Hz=22.971 GHz-cm. As can be seen in FIG. 8, for $TM_{010}$ where D=0.5 cm, $TM_{010}$ is a straight line wherein there is no resonance in the region below the line, i.e. where $f_r$ is <4.59418×10$^{10}$ GHz. Thus, a cavity having a diameter of 0.5 cm provides resonance free measurement between 0 and 20 GHz for specimens having a dielectric constant of 5 or less.

Once one realizes that resonant frequency may affect measurement accuracy for frequencies at or near the resonant frequency, and once one realizes that any such inaccuracies can be decreased or eliminated through proper cavity selection, one can choose to provide a cavity within which to test a specimen wherein the cavity has a resonant frequency outside of a range of frequencies over which the capacitance or permittivity of the specimen is to be measured. A method of obtaining the permittivity of a specimen using such a chosen cavity may include (a) placing a specimen between parallel plates within the cavity and measuring the capacitance, C, of the specimen; (b) measuring the capacitance, $C_0$, between the plates when the fixture does not contain a specimen; and (c) computing the relative real permittivity, $E_r'$, and/or the relative imaginary permittivity, $E_r''$, by calculating the ratio between the real and/or imaginary parts of C and $C_0$, or calculating loss tangent by computing the ratio of the imaginary relative permittivity to the real relative permittivity. The fixture of FIGS. 1–6 may be used in such a method.

Referring to FIG. 1, a preferred permittivity test fixture 10 comprises a metal cylindrical cavity 100 into which a thin film specimen 200 is inserted so that the permittivity of specimen 200 may be determined. Fixture 10 comprises base plate assembly 300, cap assembly 400, sleeve assembly 500, and retainer ring 600. Base plate assembly 300 comprises cylindrical base plate 310 and female pin 320. Cap assembly 400 comprises threaded plunger 410, indicator 420, and sleeve receiving portion 430. Sleeve assembly 500 comprises externally threaded cap end 510, internally threaded connector end 520, indicia portion 530, and shaft 540. Cavity 100 (also shown in FIG. 6) is defined, when fixture 10 is assembled, by base plate specimen contacting surface 311 of base plate 300, plunger specimen contacting surface 412 of plunger 410, and the cylindrical side wall of shaft 540. Base plate 310 surface 311 and plunger 410 surface 412 are the "parallel plates" between which the specimen is positioned and which are contained with cavity 100.

Figure 9:
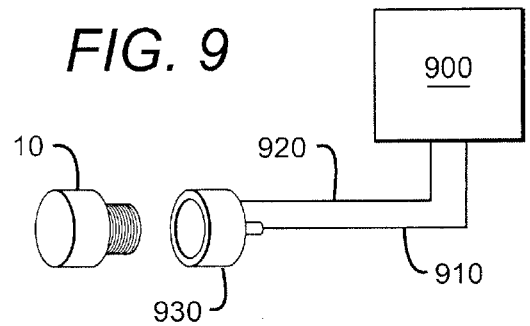
FIG. 9 is a schematic illustrating how the test fixture of FIG. 1 may be coupled to a capacitance meter.

In the preferred embodiment, base plate assembly 300, cap assembly 400, and sleeve assembly 500 are each metal and conductive, with cap assembly 400 and sleeve assembly 500 being electrically coupled to each other and to a ground (line 920 in FIG. 9) of a capacitance meter (meter 900 in FIG. 9), and base plate assembly 300 is preferably metal and electrically coupled to an output signal line (line 910 of FIG. 8) of a capacitance meter (meter 900 in FIG. 9). Retainer ring 600 is preferred to be non-conductive so as to keep base assembly 400 electrically isolated from cap assembly 400 and sleeve assembly 500. Coupling of test fixture 10 to a standard connector 930 of a capacitance meter so as to couple fixture 10 to ground and signal lines 920 and 910 is facilitated by sizing and dimensioning test fixture 10 to be coupled directly to connector 930.

Base plate assembly 300 provides the means by which specimen 200 is electrically coupled to the signal line 920 of a capacitance meter. Such a coupling is facilitated by female pin 320 which is sized, dimensions, and positioned to receive a male pin of standard connector 930 when device 10 is screwed into connector 930. Base plate 310 should be smaller than the diameter of shaft 540 to keep base plate 310 electrically isolated from the walls of shaft 540 and thus from sleeve assembly 500. The dimensions of base plate assembly may vary between embodiments as may its composition, but it is preferred that base plate assembly 300 comprise a single piece of beryllium-copper.

Cap assembly 400 seals off the end of the cavity 100 in which specimen 200 is placed. Plunger 410 extends into shaft 540 to a point adjacent to specimen 200 such that surface 412 contacts but does not compress specimen 200. By internally threading end 520 of sleeve assembly 500 and placing corresponding threads 411 on plunger 410, surface 412 can be properly positioned. Indicator 420 can be used in conjunction with indicia 530 to determine when surface 412 is properly positioned. Proper positioning will likely be related to both the desired resonant frequency of chamber 100 and the thickness of specimen 200. Although the dimensions and composition of cap assembly 400 may vary between embodiments, it is preferred that cap assembly 400 comprise a single piece of brass and that surface 412 of plunger 410 have a diameter of 0.5 cm.

Sleeve assembly 500 is preferred to be internally threaded on end 520, and externally threaded on end 510. The threads 511 on end 510 facilitate coupling fixture 10 (as previously discussed) to standard connector 930 of capacitance meter 900. For embodiments intended to be coupled to different types of connectors, end 510 and/or threads 511 may be modified or replaced by structures which facilitates coupling fixture 10 to such connectors. The dimensions and composition of sleeve 500 may also vary between embodiments, but sleeve 500 is preferred to comprise a single piece of brass and is preferred to have end 510 fit within a standard 3.5 mm female connector.

Retainer ring 600 is preferably formed from a single piece of non-conductive material such as TEFLON® and to be non-movably fixed within shaft 540 of sleeve assembly 500. Base plate 310 of base plate assembly 300 is preferably non-moveably and adhesively coupled to surface 610 of retainer ring 600. Female pin 320 of base assembly 300 extends through retainer ring 600 to provide an external electrical connection point to base plate 310.

It is contemplated that a particular embodiment of fixture 10 may be designed for a single thickness of dielectric material and a corresponding length of cavity 100. Referring to FIG. 4, an indicia portion 530 of sleeve assembly 500 may interact with indicator 420 of cap assembly 400 to indicate when surface 412 is positioned correctly. Alternatively, indicia portion 530 of sleeve assembly 500 may facilitate the use of fixture 10 for various lengths of cavity 100 by providing a scale such as that shown in FIG. 5.

A typical method of using device 10 may comprise: (a) removing cap assembly 400 from sleeve assembly 500; (b) inserting a specimen 200 to be measured into shaft 540 so that it is positioned on surface 310 of base assembly 300; (c) re-coupling cap assembly 400 to sleeve assembly 500 by inserting plunger portion 410 into shaft 540 and screwing cap assembly 500 onto sleeve assembly 500 until indicator 420 and indicia portion 530 indicate that surface 412 is adjacent to specimen 200; (d) attaching device 10 to a connector 930 of a test instrument 900 by screwing sleeve assembly 500 into connector 930 until female pin 320 is properly coupled to a male signal pin of connector 930 (attachment to connector 930 may also be accomplished prior to insertion of specimen 200); measuring the capacitance of specimen 200; (e) removing specimen 200 and by removing and replacing cap assembly 400; (f) measuring the capacitance of the free space of cavity 100 (this measurement may be done prior to measuring the capacitance of specimen 200 as well); (g) computing the permittivity of specimen 200 by computing the ratio of the appropriate portions of the capacitance of the specimen and the capacitance of the empty cavity 100.

Thus, specific embodiments and applications of permittivity test fixtures have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A parallel plate test fixture for use in measuring the capacitance of a specimen comprising an enclosed metal cavity and two parallel conductive specimen contacting surfaces positioned within the cavity; wherein the rest fixture is adapted to have a solid specimen removably positioned between the specimen contacting surfaces, the test fixture is adapted to be coupled to a capacitance meter; and the cavity is a variable volume cavity having a resonant frequency outside of a selected range.

2. The test fixture of claim 1 wherein the cavity has a resonant frequency greater than or equal to 20 GHz.

3. The test fixture of claim 2 wherein the cavity is cylindrical and has a diameter of between 0.4 cm to 0.6 cm, and the plates are separated by a distance of between 0.5 cm and 3 cm.

4. The test fixture of claim 3 further comprising a specimen to be measured wherein the specimen is sized and dimensioned to fill the volume between the two parallel conductive specimen contacting surfaces, and each of the two parallel conductive contacting surface contacts the specimen.

5. A combination comprising:
a parallel plate test fixture for use in measuring the capacitance of a specimen, the fixture having a metal cavity and two parallel conductive specimen contacting surfaces positioned within the cavity; and
a specimen to be measured wherein the specimen is sized and dimensioned to fill the volume between the two parallel conductive specimen contacting surfaces, and each of the two parallel conductive contacting surface contacts the specimen; wherein
the plates are separated by a distance of between 0.5 cm and 3 cm;
the cavity is cylindrical and has a diameter of 0.5 centimeters;
the specimen has a dielectric constant of 5 or less; and the cavity has a resonant frequency greater than 20 GHz.

6. The test fixture of claim 1 wherein the resonant frequency of the cavity is adjustable.

7. A test fixture comprising:
a metal cap assembly, the cap assembly comprising a plunger portion;
a metal sleeve assembly comprising a shaft, wherein the plunger portion of the cap assembly extends into the shaft; and
a base assembly positioned at least partially with the shaft, the base assembly comprising a specimen contacting surface opposite a specimen contacting surface of the plunger portion of the metal cap assembly;
wherein the shaft, the specimen contacting surface of the plunger portion, and the specimen contacting surface of the base assembly at least partially form an enclosed cylindrical metal cavity.

8. The test fixture of claim 7 wherein the contacting surface of the base assembly and the contacting surface of the plunger portion are separated by a distance L wherein L is between 0.5 and 3 cm.

9. The test fixture of claim 8 wherein the cavity formed is substantially cylindrical in shape.

10. The test fixture of claim 9 wherein the base assembly is electrically isolated from the cap assembly, and the cap assembly and sleeve assembly are electrically coupled.

11. The test fixture of claim 10 wherein the base assembly is electrically coupled to an output signal line of a capacitance meter and the sleeve assembly and cap assembly are electrically coupled to a ground line of the capacitance meter.

12. An assembly comprising:
a metal cap assembly, the cap assembly comprising a plunger portion;
a metal sleeve assembly comprising a shaft, wherein the plunger portion of the cap assembly extends into the shaft; and
a base assembly positioned at least partially with the shaft, the base assembly comprising a specimen contacting surface opposite a specimen contacting surface of the plunger portion of the metal cap assembly; wherein
the shaft, the specimen contacting surface of the plunger portion, and the specimen contacting surface of the base assembly at least partially form a metal cavity;
the contacting surface of the base assembly and the contacting surface of the plunger portion are separated by a distance L wherein L is between 0.5 and 3 cm;
the cavity formed is substantially cylindrical in shape;
the base assembly is electrically isolated from the cap assembly, and the cap assembly and sleeve assembly are electrically coupled;
the base assembly is electrically coupled to an output signal line of a capacitance meter and the sleeve assembly and cap assembly are electrically coupled to a ground line of the capacitance meter; and
the fixture is electrically coupled to the capacitance meter via a female 3.5 mm connector.

13. A method of determining a characteristic of a specimen comprising:
providing a cavity containing parallel conductive plates and having a resonant frequency outside of a range of frequencies over which the capacitance of the specimen is to be measured;
placing a specimen between the parallel plates and measuring the capacitance, C, of the specimen; and
measuring the capacitance, $C_0$, between the parallel plates when it does nor contain a specimen;
wherein the cavity is a variable volume cavity, and providing the cavity includes adjusting the volume of the cavity to cause the resonant frequency of the cavity to be outside of a range of frequencies over which the capacitance of the specimen is to be measured.

14. The method of claim 13 wherein the characteristic to be determined is the relative real permittivity, $E_r'$, and C and $C_0$ have both real and imaginary parts, the characteristic being determined by dividing the real portion C by the real portion of $C_0$.

15. The method of claim 13 wherein the characteristic to be determined is the relative imaginary permittivity $E_r''$, and C and $C_0$ have both real and imaginary parts, the characteristic being determined by dividing the imaginary portion C by the imaginary portion of $C_0$.

16. The method of claim 13 wherein the characteristic to be determined is the loss tangent and C and $C_0$ have both real and imaginary parts, the characteristic being determined by computing the ratio of the imaginary relative permittivity to the real relative permittivity.

17. The method of claim 13 further comprising the step of realizing that the resonant frequency of the cavity may affect measurement accuracy for frequencies at or near the resonant frequency.

18. A method for determining a characteristic of a specimen comprising:

providing a parallel plate test fixture coupled to a signal source wherein the fixture comprises a metal cavity enclosing two parallel conducting surfaces;

causing the signal source to generate a signal having a frequency greater than 1.8 GHz and measuring frequency dependent characteristic of the specimen.

19. The method of claim 18 further comprising inserting a specimen in the test fixture between the two parallel conducting surfaces prior to measuring a frequency dependent characteristic of the specimen, and removing the specimen from the test fixture after measuring a frequency dependent characteristic of the specimen.

* * * * *